United States Patent [19]
Uno et al.

[11] Patent Number: 5,726,752
[45] Date of Patent: Mar. 10, 1998

[54] SAMPLE CELL OF MULTIPLE REFLECTION TYPE

[75] Inventors: Masahiro Uno; Mutsumi Nagumo; Hideyuki Tanaka, all of Tokyo, Japan

[73] Assignee: Fuji Electric Co., Ltd., Kawasaki, Japan

[21] Appl. No.: 688,731

[22] Filed: Jul. 31, 1996

[30] Foreign Application Priority Data

Aug. 7, 1995 [JP] Japan .................. 7-200149

[51] Int. Cl.$^6$ ..................... G01N 21/01; G01N 21/00
[52] U.S. Cl. ................ 356/246; 356/244; 356/440; 359/850; 359/861
[58] Field of Search ................ 356/244, 246, 356/51, 440, 437, 409, 436; 359/850, 853–859, 861, 863, 867, 869, 894; 350/293, 320, 189, 192, 294, 96.32; 250/575, 343, 345, 573, 574, 353, 428, 435, 437, 438

[56] References Cited

U.S. PATENT DOCUMENTS

| | | | |
|---|---|---|---|
| 2,212,211 | 8/1940 | Pfund | 73/51 |
| 3,449,565 | 6/1969 | Barringer | 416/64 |
| 3,726,598 | 4/1973 | Gilby | 356/244 |
| 3,916,195 | 10/1975 | Burch et al. | 250/345 |
| 4,035,963 | 7/1977 | Gilby | 51/324 |
| 4,209,232 | 6/1980 | Chernin | 350/294 |
| 4,225,232 | 9/1980 | Boisde et al. | 356/246 |
| 4,291,988 | 9/1981 | Dixon, Jr. et al. | 356/437 |
| 4,749,276 | 6/1988 | Bragg et al. | 356/246 |
| 4,934,816 | 6/1990 | Silver et al. | 356/409 |
| 5,009,493 | 4/1991 | Koch et al. | 350/619 |
| 5,065,025 | 11/1991 | Doyle | 250/343 |
| 5,068,798 | 11/1991 | Heath et al. | 364/497 |
| 5,220,402 | 6/1993 | Harvey | 356/246 |
| 5,222,389 | 6/1993 | Wong | 73/31 |
| 5,270,945 | 12/1993 | Heath et al. | 364/497 |
| 5,440,143 | 8/1995 | Carangelo et al. | 250/573 |
| 5,459,566 | 10/1995 | Pearson et al. | 356/246 |

FOREIGN PATENT DOCUMENTS

| | | |
|---|---|---|
| 2223691 | 10/1974 | France . |
| 1948193 | 4/1971 | Germany . |
| 2321405 | 11/1973 | Germany . |
| 7429150 | 12/1974 | Germany . |
| 2511771 | 9/1976 | Germany . |
| 2905079A1 | 10/1979 | Germany . |
| 2912233 | 10/1979 | Germany . |
| 3700580A1 | 7/1988 | Germany . |
| 3390532 | 8/1989 | Germany . |
| 3152972 | 12/1989 | Germany . |
| 3942325A1 | 6/1991 | Germany . |
| 4002436A1 | 8/1991 | Germany . |
| 4434814 | 4/1996 | Germany . |

OTHER PUBLICATIONS

Edwards; T.H.: Multiple–Traverse Absorption Cell Design; Journal of the Optical Society of America, vol. 51, No. 1, 1961, pp. 98–102.

(List continued on next page.)

*Primary Examiner*—Frank G. Font
*Assistant Examiner*—Michael P. Stafira
*Attorney, Agent, or Firm*—Greer, Burns & Crain, Ltd.

[57] ABSTRACT

A sample cell of the multiple reflection type is used for analyzing a sample in the same cell. In the sample cell, incident light is reflected a plurality of times. The sample cell includes a mirror plate including a light incident window for introducing the incident light into the sample cell, a first concave mirror, and a light exit window for outputting the incident light form the sample cell. A side plate including a second concave mirror reflects the incident light to the first concave mirror and a third concave mirror for reflecting the incident light reflected by the first and second concave mirrors to the light exit window. The cell also includes a frame for fixing the mirror plate and the side plate so that the distances between the first concave mirror and the second and third concave mirrors are fixed at a distance equal to the radius of curvature of the three concave mirrors.

36 Claims, 7 Drawing Sheets

OTHER PUBLICATIONS

Bragg, S.L.; Wiswall, C.E.: Long-path absorption cell for use with condensable samples; Rev. Sci. Instrum. 57; Jan. 1986, pp. 13–16.

Brügel, Dr. Werner; Einführung in die ultrarotspektroskopie; Dr. Dietrich Steinkopff Verlag; Darmstadt, 1962; pp. 200–205.

Schrader, Berhnhard; Infrared and Raman Spectroscopy; Winheim, 1995; pp. 126–131.

Aref'ev, V.; Optical multipath vessel for investigating absorption by artifical atmosphere; Instruments and Experimental Techniques, vol. 17, No. 1, 1974; pp. 227–230.

Macleod, H.A.: Thin–Film optical filters; Adam Hilger Ltd., Bristol, 1986; pp. 4–10.

JP 61–91542 A; Patent Abstracts of Japan; P–496; Sep. 11, 1986; vol. 10, No. 266.

SAMPLE CELL OF MULTIPLE REFLECTION TYPE

BACKGROUND OF THE INVENTION

1. Field of the Invention

The present invention relates to a multiple reflection sample cell used in gas analyzers such as an infrared gas analyzer, and more specifically to of a multiple reflection type sample cell in which a long optical path is obtained in a limited space.

2. Description of the Related Art

An analyzer, such as a nondispersive infrared gas analyzer, uses a detector which is sensitive in an absorption wavelength region thereof a specific gas component to be analyzed. The nondispersive gas analyzer is widely used in chemical or industrial processes for continuously measuring concentrations of the specific component. For facilitating stable measurements using the nondispersive gas analyzer, the optical density, which is the product of the absorption coefficient and concentration of the component to be analyzed and the optical path length of the sample cell, should be within an appropriate range. When the concentration of the component to be analyzed is extremely low, the optical path length of the sample cell should be long enough to bring the optical density within the appropriate range. However, the long optical path length prevents the gas analyzer from being minimized and being more practical.

A sample cell with a long optical path length is used for detecting and measuring the low concentration component by scanning a wavelength region for which the component exhibits a light absorption, in an infrared spectrophotometer or the like, which is provided with a spectroscopic function and used mostly in testing or research. For obtaining a long path length in a limited space of the spectrophotometer, a sample cell the multiple reflection type 10, as shown in FIGS. 1A through 1D, was proposed by J. U. White (hereinafter referred to as a White cell). The White cell 10 utilizes multiple reflections among three concave mirrors with the same curvature.

The operations and principle of the White cell 10 are described in detail in the following documents 1) through 3). The principle and structure of the White cell 10 will be briefly reviewed below to facilitate understanding of the present invention.

1) J. U. White, J. Opt. Soc. Am., vol 32,285 (1942)

2) J. U. White, N. L. Alperr, A. D. DeBell, J. Opt. Soc. Am., vol 45,154 (1955)

3) P. Hannon, Opt. Engineering, vol 28,1180 (1989)

Figure 1A:
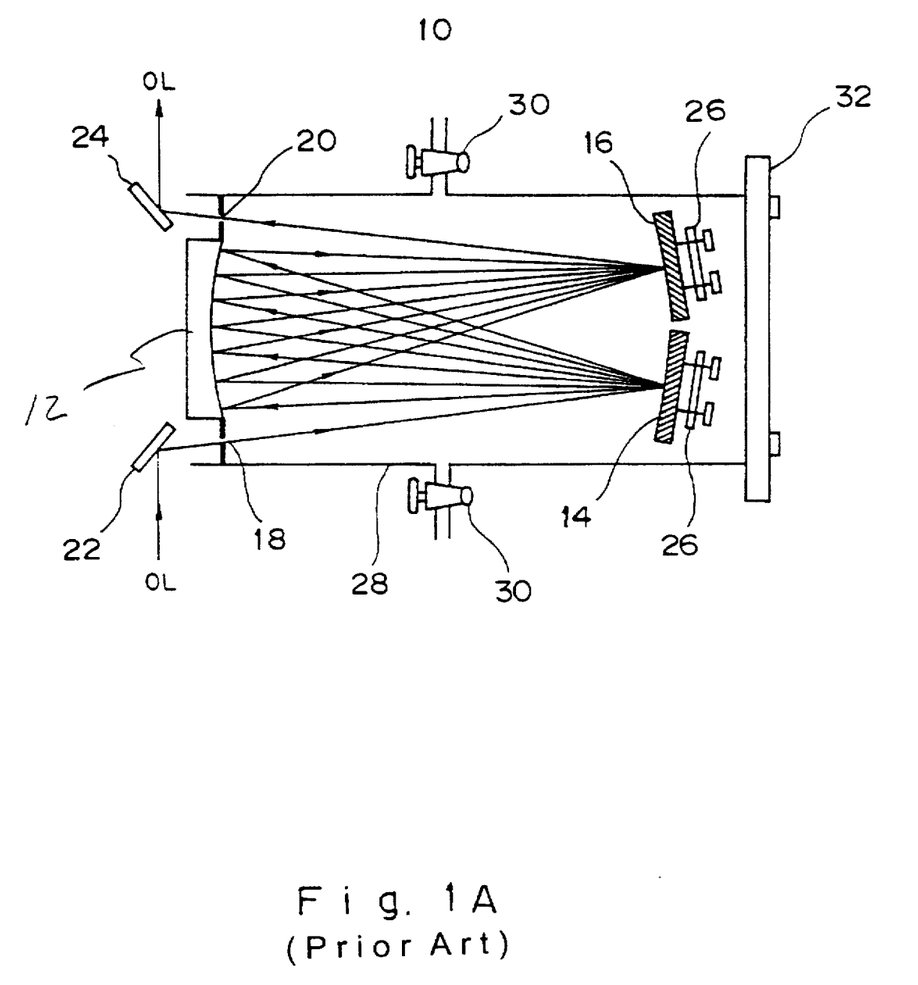
FIG. 1A shows a cross-sectional view of a conventional White cell.
Figure 1B:
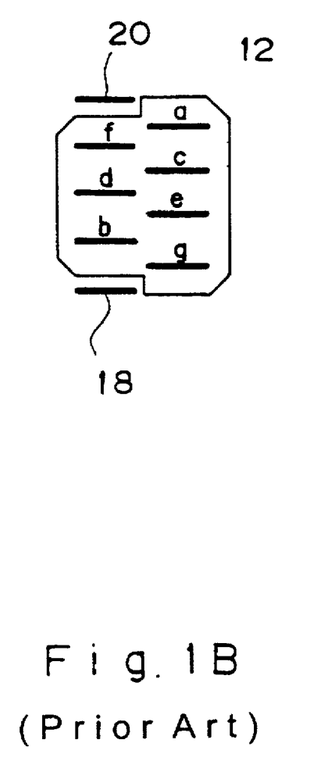
FIG. 1B shows a front view of the central concave mirror of the White cell.
Figure 1C:
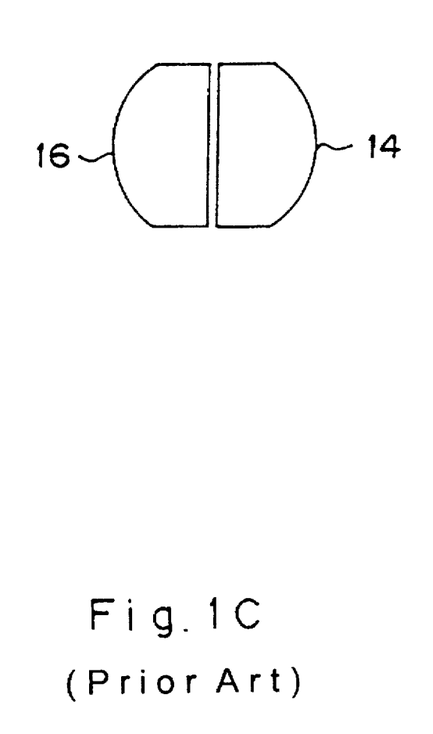
FIG. 1C shows a front view of the incident focusing mirror and the exit focusing mirror of the White cell.

Referring now to FIG. 1A, three concave mirrors, a central concave mirror 12, an incident focusing mirror 14 and exit focusing mirror 16 have the same radius of curvature R. FIGS. 1B and an 1C show front views of the central concave mirror 12 and the focusing mirrors 14 and 16, respectively. The central concave mirror 12 and the focusing mirrors 14 and 16 are arranged in such a way that the reflection planes thereof, facing opposite to each other, are spaced by the radius of curvature R. A light incident window 18, consisting of a slit or a small hole, is disposed for introducing a light beam into a White cell 10. The incident focusing mirror 14 facing opposite to the window 18 focuses an image from the light incident window 18 onto the reflection plane of the central concave mirror 12 arranged adjacent to the window 18. The exit focusing mirror 16 focuses the image formed on the central concave mirror 12 again onto the central concave mirror 12.

According to the concave mirror arrangement described above, a light beam incident from the light incident window 18 is reflected by the incident focusing window 14 to the central concave mirror 12, and then reflected again to the exit focusing mirror 16, which again reflects the light beam to the central focusing mirror 12. In this way, the incident light beam bounces back and forth between the central concave mirror 12 and the focusing mirrors 14 and 16 through points a to g, which also show images of the light incident window 18, on the central concave mirror 12, as shown in FIG. 1B, and finally exit from the White cell 10 through a light exit window 20.

In mounting a White cell 10 with a large volume on a sample cell mounting portion of an infrared spectrophotometer or the like, an incident light guide mirror 22 is disposed on a measuring light path OL of the infrared spectrophotometer for deflecting the light beam traveling on the light path OL to light incident window 18, as shown in FIG. 1A. An exit light guide mirror 24 is also disposed on the light path OL for returning an outgoing light beam from the light exit window 20 of the White cell back onto the light path OL of the spectrophotometer. By using a concave mirror or a lens (not shown in the figure), the light beam emitted from a light source (neither shown in the figure) is collected to the light incident window 18. Therefore, the window 18 functions as a light source inside the White cell 10.

Figure 1D:
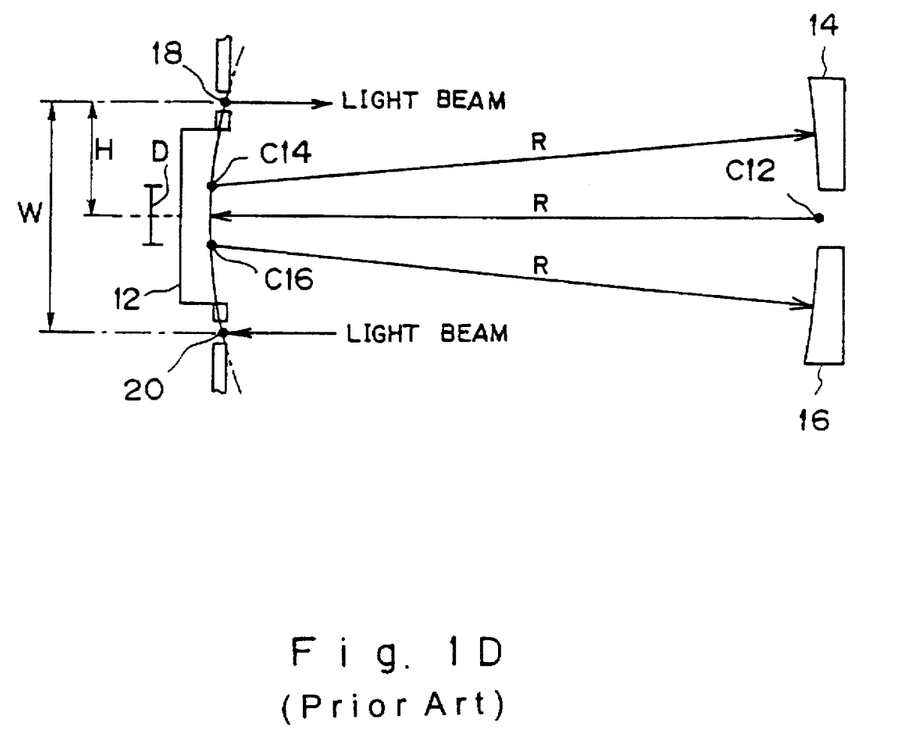
FIG. 1D shows the principle of the White cell.

Optical formulae which hold for the White cell 10 as constructed above will be briefly explained with reference to symbols described in FIG. 1D. The following image formation formula (1) holds on the basis of the principle of geometrical optics between an object located near an optic axis, for which the aberration of a concave mirror having a radius of curvature R can be neglected, and its image.

$$1/A + 1/B = 2/R = 1/F \quad (1)$$

Here, "A" represents the distance from the center of the concave mirror and an object point, "B" the distance from the center of the concave mirror and an image point, "R" the radius of curvature of the concave mirror, and "F" the focal length of the concave mirror which is equal to R/2.

When the distance A is equal to the radius of curvature R of the concave mirror, the distance B is also equal to R, and an image at the object point is focused on a point symmetrical with respect to the optic axis of the concave mirror.

Since the light incident window 18 is arranged in a position spaced for a distance equal to the radius of curvature R of the incident focusing mirror 14 from the reflection plane of the incident focusing mirror 14 facing opposite thereto, the image at the light incident window 18 is focused on a position spaced for a distance equal to the radius of curvature R, that is on the reflection plane of the central concave mirror 12. Further, the image at the window 18 focused on the central concave mirror 16 is then focused by the exit focusing mirror 16 again on a position of the central concave mirror 12 determined by the arrangement of the exit focusing mirror 16.

By repeating the above described processes, the incoming light beam from the light incident window 18 exits the White cell 10 from the light exit window 20 after forming a plurality of images a to g of the light incident window 18, which are arranged depending on a spacing D between the centers of curvature C14 of the incident focusing mirror 14 and C16 of the exit focusing mirror 16. If we call the number of paths of the light beam in the White cell 10 "n", then the number of reflections is "n−1", and the following equations (2) and (3) hold.

$$R = L/n \quad (2)$$

$$H = nD/4 \quad (3)$$

Here, "R" is the radius of curvature of each of the incident, central and exit concave mirrors (12, 14, and 16), "L" a required optical path length, "H" the distance between the centers of the central concave mirror 16 and the light incident window 18, and "D" the distance between the centers of curvature C14 and C16 of the incident and exit focusing mirrors 14 and 16. On the central concave mirror, $n/2-1$ pieces of images of the light incident window 18 are aligned with a spacing D in-between. The spacing W between the light incident and exit windows 18 and 20 is given by the following equation (4).

$$W = nD/2 \quad (4)$$

Since the above described relations hold, when the number of paths is set at a multiple of 4, the light exit window 20 is arranged on the symmetrical position to the light incident window 18 with respect to the central reflection mirror 12.

Since the number of paths n is set at 16 in FIG. 1A, the incident light beam from the light incident window 18, which functions as a light source, focuses seven images a through g of the window 18 on the central concave mirror 12 by 15 reflections. Finally, the incident light beam focuses the image of the light incident window 18 on the light exit window 22, and returns to the measuring optical path OL of the spectrophotometer outside the White cell 10.

Though a long optical path length is obtained by setting a large number of reflections, it is necessary to precisely arrange each of the precisely machined concave mirrors at the predetermined position with a predetermined orientation so that the incident light beam to the White cell may be emitted properly and stably from the White cell after the predetermined times of reflections. To facilitate this in the conventional White cell, mounted in the sample cell portion of the spectrophotometer for detecting a trace component in a sample to be analyzed, the incident and exit focusing concave mirrors 14 and 16, mounted on respective fine adjusting mechanisms 26 for adjusting the respective positions and optic axis directions thereof, are arranged in an end portion of a cylindrical vessel 28. The vessel 28 has a sample cock 30 thereon for introducing a sample to be analyzed. After adjusting and fixing the optical orientations of the concave mirrors, the vessel 28 is sealed airtightly with a cover 32 to form a White cell.

Since the conventional White cell structure has been developed for spectrophotometers for testing and research to secure an optical path length exceeding 100 m by many reflections, fine adjustment of the optical system is necessary. Since it is necessary to adopt a structure which facilitates arranging the concave mirrors mounted on the respective adjusting mechanisms, the sample cell inevitably becomes bulky with a wide dead space left therein.

On the other hand, the required optical path length is around 1 m in the sample cell of the nondispersive infrared gas analyzers for measuring a low concentration component. The sample cell of the nondispersive infrared gas analyzer should be small enough, with minimal dead space left therein, to replace the sample gas quickly and to attain a quick response of analysis. Therefore, it is impossible to apply the conventional White cell structure without modifying it to the nondispersive gas analyzers for measuring a low concentration component.

SUMMARY OF THE INVENTION

In view of the foregoing, it is an object of the invention to provide a small sample cell of multiple reflection type with minimal dead space left therein which is easy to manufacture and applicable advantageously to infrared gas analyzers and the like.

A sample cell of the multiple reflection type according to the invention, in which incident light is reflected a plurality of times, is for analyzing a sample of, for example, gas injected in the sample cell. The sample cell comprises: a mirror plate including a light incident window for introducing the incident light into the sample cell, a first concave mirror, and a light exit window for outputting the incident light from the sample cell; a side plate including a second concave mirror for reflecting the incident light to the first concave mirror, and a third concave mirror for reflecting the incident light reflected by the first and second concave mirrors to the light exit window; and a frame for fixing the mirror plate and the side plate so that the distances between the first concave mirror and the second and third concave mirrors are fixed.

The distance between the mirrors corresponds to the radius of curvature of the first, second and third concave mirrors, the second concave mirror focuses an image of the light incident window on the first concave mirror, and the third concave mirror focuses on the light exit window an image focused on the first concave mirror.

The second and third concave mirrors may be integrated with the side plate in one piece. The frame may occupy the immediate outside of the envelope region of the incident light in the sample cell. The mirror plate, the side plate, and/or the frame may be made of aluminum or aluminum alloy. A chrome (Cr) layer, a silicon dioxide ($SiO_2$) layer, and a gold (Au) layer may be formed in this order on an inside wall of the sample cell.

The mirror plate, the side plate, and the frame may be replicas duplicated using a molding die, and at least two of the mirror plate, the side plate and the frame may be molded in one piece.

The light incident window and the light exit window may comprise a transparent substrate and a transparent layer formed on the transparent substrate, refractive indices of the transparent substrate and the transparent layer being different from each other, and the transparent substrate and the transparent layer functioning as one of an optical band pass filter, an optical low-pass filter and an optical high-pass filter.

The light incident window and the light exit window may comprise a plurality of transparent layers having different refractive indices and functioning as one of an optical band pass filter, an optical low-pass filter and an optical high-pass filter.

The mirror plate may be made of a material transparent with respect to wavelengths of light used for an analysis of the sample, and a layer of a material having one of high reflectivity and high refractive index may be formed on a portion of the mirror plate corresponding to the first concave mirror. In this case, the sample cell may further comprise an antireflection film, having a refractive index smaller than that of the mirror plate, formed on a portion of the mirror plate corresponding to the light incident window or the light exit window.

The sample cell may further comprise, a transparent layer formed on a portion of the mirror plate corresponding to the light incident window or the light exit window, refractive indices of the transparent layer and the mirror plate being different from each other, and the transparent layer and the portion of mirror plate functioning as one of an optical band pass filter, an optical low-pass filter and an optical high-pass filter.

The sample cell may further comprise a plurality of transparent layers formed on a portion of the mirror plate corresponding to the light incident window or the light exit window, refractive indices of the plurality of transparent layers being different from each other, and the plurality of transparent layers functioning as one of an optical band pass filter, an optical low-pass filter and an optical high-pass filter.

A manufacturing method of a sample cell of multiple reflection type in which incident light is reflected a plurality of times for analyzing a sample in the sample cell, according to the invention includes the steps of: manufacturing the mirror plate; manufacturing the side plate; and manufacturing the frame.

The step of manufacturing the side plate may include a step of making the second and third concave mirrors by cutting the side plate using a lathe. The frame may be manufactured so that an inside space of the frame broadens along the direction from the mirror plate to the side plate. The manufacturing method may further include the step of forming a chrome (Cr) layer, a silicon dioxide ($SiO_2$) layer and a gold (Au) layer in this order on an inside wall of the sample cell.

The manufacturing method may further include the steps of, attaching a transparent plate to the light incident window or the light exit window, and forming, on the transparent plate, the transparent layer having a refractive index different from that of the transparent plate. The manufacturing method may further include the step of forming, at the light incident window or the light exit window, the plurality of transparent layers having refractive indices different from each other.

The mirror plate may be made of a material transparent with respect to wavelengths of light used for an analysis of the sample, and the manufacturing method may further include the step of forming a layer of a material having one of high reflectivity and high refractive index, on a portion of the mirror plate corresponding to the first concave mirror.

In this case, the manufacturing method may further include the step of forming an antireflection film, having a refractive index smaller than that of the mirror plate, on a portion of the mirror plate corresponding to the light incident window or the light exit window.

The manufacturing method may further include the step of forming a plurality of transparent layers on a portion of the mirror plate corresponding to the light incident window and/or the light exit window, refractive indices of the plurality of transparent layers being different from each other.

Since the required optical path length is around 1 m in the sample cell of the nondispersive infrared gas analyzers for measuring a low concentration component, a sample cell of multiple reflection type can be constructed on the basis of the principle of the White cell within allowable dimensions for constituent parts of the process analyzers by setting the number of paths at around 12 at most and the radius of curvature of the concave mirrors at around 10 cm.

For realizing the sample cell of multiple reflection type having the optical requirements such as those described above, the sample cell of multiple reflection type according to the invention is made by forming three concave mirrors and incident and exit windows with the respective parameters satisfying the predetermined optical conditions on the end wall parts of the sample cell, without disposing the adjusting means for adjusting the positions and orientations of the concave mirrors, and by tightly fixing the end wall parts on the respective ends of the frame for defining the spacing between the concave mirrors and for constituting the side wall of the sample cell. Any dead space is avoided in the sample cell by occupying a space immediately beyond an envelope region of the light beam in which the light beam passes in the sample cell with the side wall part.

The structure and manufacturing process of the sample cell according to the invention are simplified by using a material, transparent in the wavelength region for analytical measurement, for the mirror plate on which the central concave mirror and the light incident and exit window portions are formed so that any additional machining may not be necessary for forming the light incident and exit windows.

Furthermore, antireflection films or filters for selectively passing a specific wavelength are formed on the mirror plate by coating single or multiple transparent layers having refractive indices different from one another and from that of the mirror plate material.

DESCRIPTION OF THE PREFERRED EMBODIMENT

Embodiments according to the present invention will be described hereinafter with reference to the drawings.

[First Embodiment]

Figure 2:
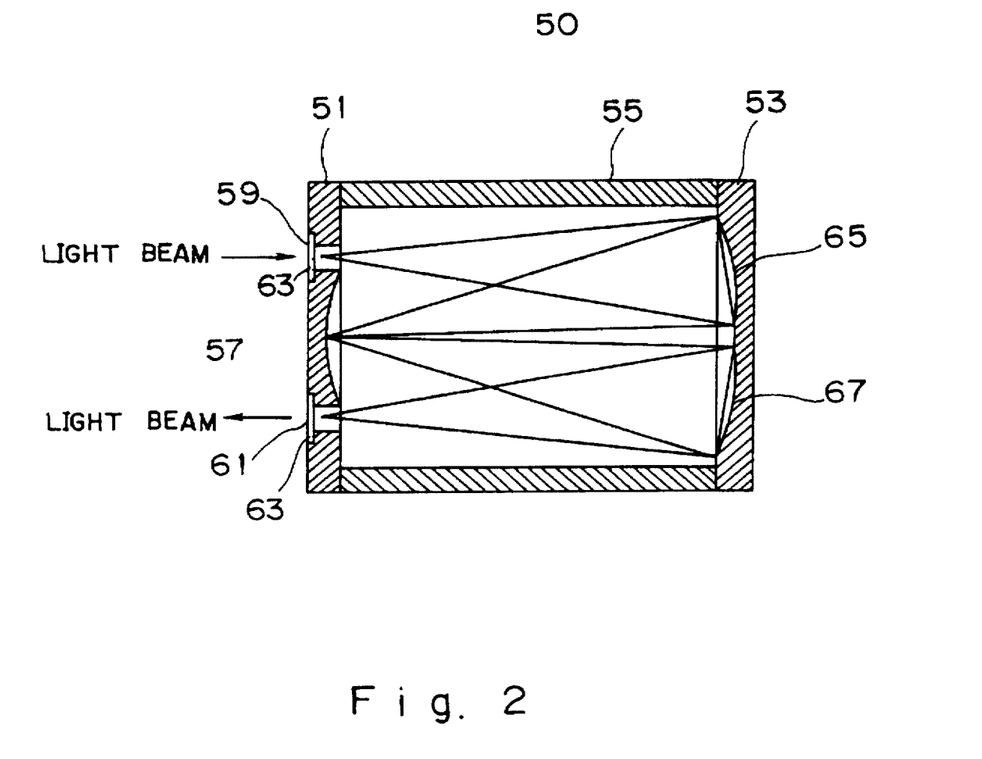
FIG. 2 is a cross-sectional view of a first embodiment of a sample cell of multiple reflection type according to the invention.

FIG. 2 is a cross-sectional view of a first embodiment of a sample cell of multiple reflection type according to the invention. The sample cell 50 of FIG. 2 is devised to be applicable to the nondispersive infrared gas analyzers for measuring a low concentration chemical component. This sample cell is constructed so that its number of paths is 4: an incident light beam goes out of the cell after being reflected three times, once by each concave mirror.

As shown in FIG. 2, the sample cell 50 comprises a mirror plate 51, a side plate 53, and a frame 55. A central concave mirror 57 is formed on or in the central portion of the inside face of the mirror plate 51, and openings for a light incident window 59 and a light exit window 61 are bored on both sides of the mirror plate 51, for introducing a light beam into and outputting the light beam from the sample cell 50, respectively.

Window members 63 of, for example, calcium fluoride plates transparent in the infrared region are mounted on the openings by adhesion, or such bonding techniques. For enhancing selectivity to a specific component to be analyzed, it is effective to use an optical band pass filter of a low-pass filter or a high-pass filter, which is formed by depositing multiple optically transparent layers on a transparent substrate, for the window members 63. The transparent layers preferably exhibit different optical refractive indices from one another and from that of the substrate.

An incident focusing mirror 65 and an exit focusing mirror 67, which are formed on or in the inside face of the side plate 53, guide the light beam which has come in from the light incident window 59 to the light exit window 61 via the central convex mirror 57, which is unitarily formed (formed in one piece) on or in the central part of the inside face of the mirror plate 51. The incident focusing mirror 65 and the exit focusing mirror 67 are also formed in one piece on the central part of the side plate 53.

The three concave mirrors of the central concave mirror 57 and the incident and exit focusing mirrors 65 and 67 are so formed as to have the same radius of curvature R. The frame 55 spaces the mirror plate 51 and the side plate 53 so that the reflection planes of the incident and exit focusing mirrors 65 and 67 are arranged on the radius of curvature R of the central concave mirror 57. The frame 55 constitutes the side wall of the sample cell 50.

The process for determining the optical parameters of the sample cell 50 of multiple reflection type of FIG. 2 will be explained below.

The optical path length L in the sample cell 50, which gives an optical density for facilitating stable analytical measurement, is determined on the basis of the given conditions, i.e., the object component of analysis and the concentration range thereof. The conditions of the light beam radiated to the sample cell 50 from dimension source, i.e. dimension of the light incident window 59 of the sample cell 50 and solid angle of the incident light beam, are determined based on the characteristic parameters of the light detector such as sensitivity and the size of the light receiving area.

Since the number of paths is set at the minimum number, i.e., 4 for ease of manufacture, the radius of curvature R of the three concave mirrors 57, 65 and 67 is determined by putting this number of paths and the optical path length L of this sample cell 50 into the foregoing equation (2).

When the sample cell is subjected to severe dimensional limitations, the allowable maximum radius of curvature of the concave mirrors is temporarily fixed, an appropriate number of paths is selected by dividing the optical path length L by the temporarily fixed radius of curvature, and the radius of curvature is finally determined based on the selected number of paths. When the selected path number is extremely large, it will be difficult to manufacture a sample cell on the basis of this number of paths.

Since one single image of the light incident window 59 is focused on the central concave mirror 57 when the path number is 4 as in the first embodiment, the aperture of the central concave mirror 57 is selected to be as large as to cover the focused image of the light incident window 59.

The aperture of the incident focusing mirror 65 is determined based on the solid angle of the incident light beam and the determined radius of curvature R of the concave mirrors, so that the incident focusing mirror 65 receives the light within the solid angle range of the light beam radiated from the light incident window 59 into the sample cell 50 and reflect the received light beam toward the central concave mirror 57. The aperture of the exit focusing mirror 67 may be set at the same value with that of the incident focusing mirror 65, since the focused image of the light incident window 59 on the central concave mirror 57 functions for the exit focusing mirror 67 as the light incident window 59 does for the incident focusing mirror 65.

Once the aperture of the central concave mirror is set, the value of the position H of the light incident window 59 disposed adjacent to the central concave mirror 57 is set. By putting the set position H and the path number (n=4) into equation (3), the spacing D between the centers of curvature C65 and C67 of the focusing mirrors 65 and 67 is determined. In this embodiment, the position H denotes a distance between the centers of the central concave mirror 57 and the light incident window 59 or the light exit window 61.

Since multiple images are formed with the spacing D between adjoining images on the central concave mirror 57, as explained earlier in connection with equation (3) when the number of paths is equal to or more tan 4, it is necessary to determine the values of the aperture of the central concave mirror 57 and the distance D so that the images may not overlap one another on the central concave mirror 57.

Thus, the basic parameters of the parts and components of a multiple-reflection cell are determined based on the given conditions. Then, the multiple-reflection cell, which exhibits predetermined performance, is manufactured by assembling the parts and components machined by the machines which facilitate realizing the basic parameters with high precision.

In the embodiment of FIG. 2, the central concave mirror 57, the light incident window 59, and the light exit window 61 are formed on the mirror plate 51, the incident and exit focusing mirrors 65 and 67 are formed on the side plate 53, and the frame 55, as the side wall of the sample cell, holds the mirror plate 51 and the side plate 53 at the right positions. The mirror plate 51, the side plate 53, and the frame 55 form the multiple-reflection sample cell. When these parts are made of aluminum, which is easily machinable, the concave mirrors formed on the mirror and side plates 51 and 53 are machined, e.g., with an ultra precision CNC lathe with air bearings which can very precisely machine a curved surface according to the numeric values which define the curved surface. The radius of curvature R of the concave mirrors, the distance D between the centers of curvature, and the apertures of the concave mirrors are input to the lathe prior to the machining. The other parts and portions may be machined with an ordinary NC milling machine.

Since the curved surfaces with specified dimensions and orientations can be realized with high precision by machining with the ultra precision CNC lathe having air bearings, it becomes unnecessary to finely adjust the positions and orientations of the incident and exit focusing mirrors. Thus, the incident and exit focusing mirrors can be formed on the side plate 53 in one-piece with the side plate 53.

The sample cell according to the invention also comprises a cock which corresponds to the sample cock 30 shown in FIG. 1A, but is not shown in the figure for brevity.

[Second Embodiment]

Figure 3:
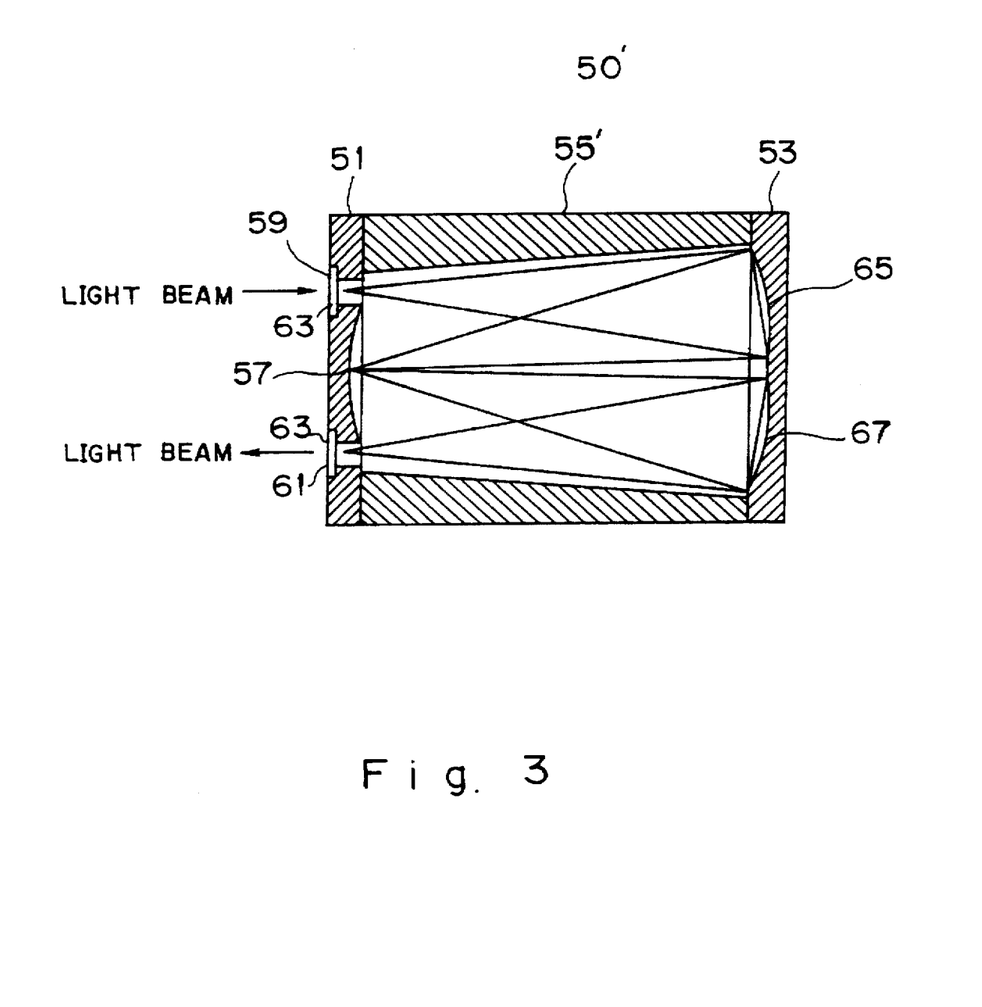
FIG. 3 is a cross-sectional view of a second embodiment of a sample cell of multiple reflection type according to the invention.
Figure 4:
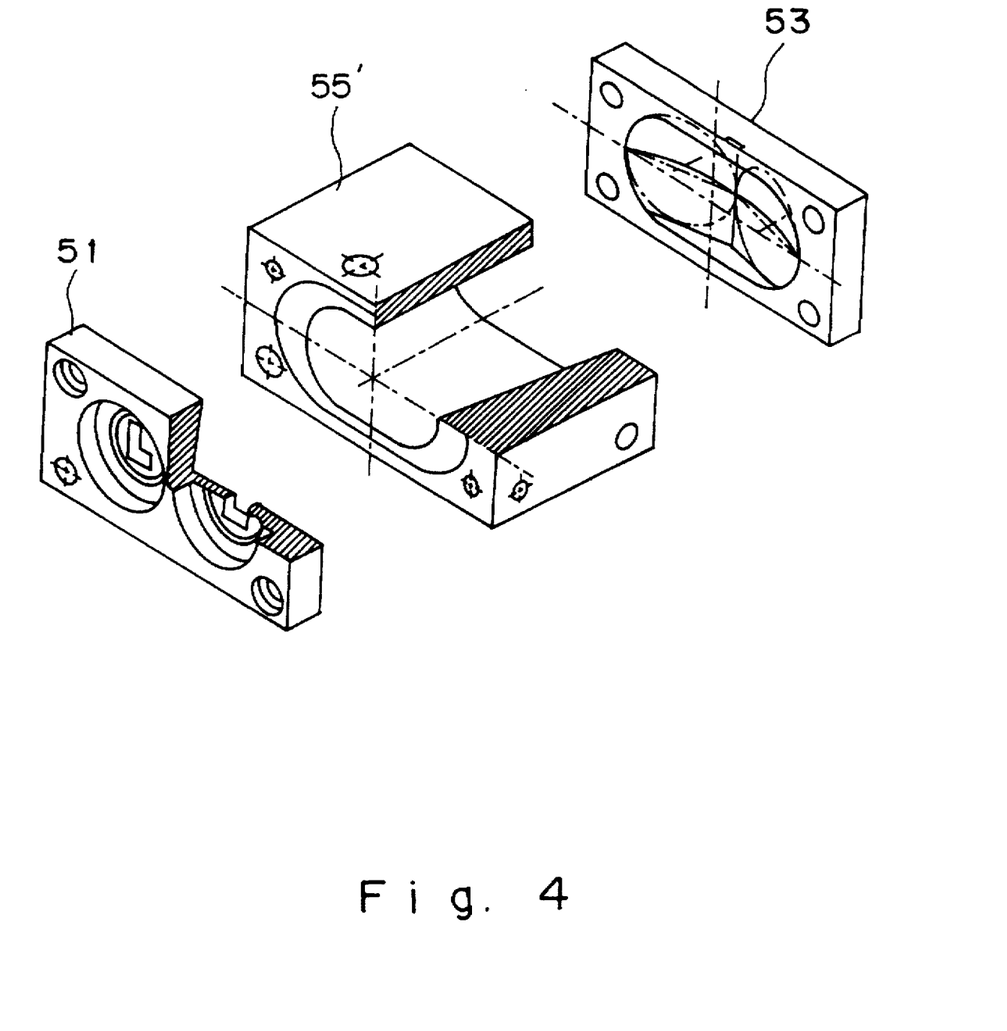
FIG. 4 is an exploded isometric view of the sample cell of the second embodiment.

FIG. 3 is a cross-sectional view of a second embodiment of a sample cell 50' of multiple reflection type according to the invention, and FIG. 4 is an exploded isometric view of the sample cell 50' of multiple reflection type shown in FIG. 3. In these figures, same reference numerals denote the same members in FIGS. 2 through 4.

The sample cell 50' comprises the mirror and side plates 51 and 53, which are the same as those of the first embodiment, and a frame 55', which is made (machined) so that the frame 55' occupies a space immediately beyond of the envelope region within which the light beam passes, as shown in FIGS. 2 and 3.

When the frame 55' is assembled with the mirror and side plates 51 and 53, the dead space inside the sample cell 50' is minimized. Guide pins and insertion holes are preferably disposed on the constituent parts for accurately fixing the mutual positions of the constituent parts during assembly.

When each part of the sample cell is made of easily machinable aluminum as in the embodiments of the invention, a chromium (Cr) layer, a silicon dioxide ($SiO_2$) layer and a gold (Au) layer are preferably deposited in the order of the above description by a film deposition method of, for example, vacuum deposition or sputtering, on the inside surface of each constituent part after the part has been machined to the predetermined dimensions thereof. By forming the chromium (Cr) and silicon dioxide ($SiO_2$) layers on the inside wall of the sample cell, the corrosion resistance against gas introduced into the sample cell is obtained, and high reflectivity on the concave mirrors 57, 65, and 67 is realized by the Au layer.

When it is necessary to manufacture many sample cells with the same dimensions, it is not efficient to manufacture such sample cells by forming each constituent part of the sample cells by a cutting method and then assembling them. Replicas of a specific type of sample cell may be manufactured efficiently with low manufacturing costs by compression-molding PC, PPO, or PPC (engineering plastic) individual or composite parts, having a plurality of optical elements integrated therein. Replicas of the individual or composite parts may be manufactured by die casting a metal or metals with relatively low melting points in respective molding dies.

For example, the mirror plate 51 and the frame 55 of the sample cell with the cross section shown in FIG. 3 can be integrated into a unitary by compression-molding these parts, since the slant inner face of the frame 55 facilitates pulling out the molded unitary from the molding die. The molding dies for this unitary and for the side plate 53 may be fabricated, e.g., by the foregoing CNC lathe with air bearings. The reflecting and shading planes of the parts, including the concave mirrors 57, 65, and 67, formed by compression molding are covered with a film of gold (Au) or a light reflecting material by a film deposition method of, for example, sputtering.

The size of each element of the sample cell has a dependence on the optical path length required of the sample cell. The optical path length of the sample cell of the embodiment is, for example, 500 mm or 1000 mm, which is not more than about 1000 mm. Using the two samples with 500 mm and 1000 mm optical path lengths, almost every kind of gas may be analyzed by the infrared gas analyzer. The sample cells of this embodiment are suitable for an analysis using a light beam with a wavelength of 2 through 15 micron (µ).

The sizes of the elements of the sample cell having 500 mm optical path length are as follows:

The radius of curvature of each of the concave mirrors 57, 65 and 67: SR 42.1±0.1 mm;

The slant of degree of the inner face of the frame 55': 13.5°;

The size of the light incident window 59: 2.5×6 mm;

The size of the light exit window 61: 4.3×6 mm;

The size of the mirror plate 51: 32×58×5 t mm;

The size of the side plate 53: 32×58×7.5 mm; and

The size of the outside of the sample cell 50': 32×58×36 mm.

The size of the light incident window 59 is smaller than that of the light exit window 61. The smaller size of the light incident window 59 makes an effect of an optical diaphragm, which improves noise characteristics.

The sizes of the elements of the sample cell having 1000 mm optical path length are as follows:

The radius of curvature of each of the concave mirrors 57, 65 and 67: SR 84.2±0.1 mm;

The slant of degree of the inner face of the frame 55': 13.5°;

The size of the light incident window 59: 5.4×8 mm;

The size of the light exit window 61: 5.4×8 mm;

The size of the mirror plate 51: 62×79×6.5 t mm;

The size of the side plate 53: 62×100×12.5 mm; and

The size of the outside of the sample cell 50': 62×100×73 mm.

[Third Embodiment]

Figure 5:
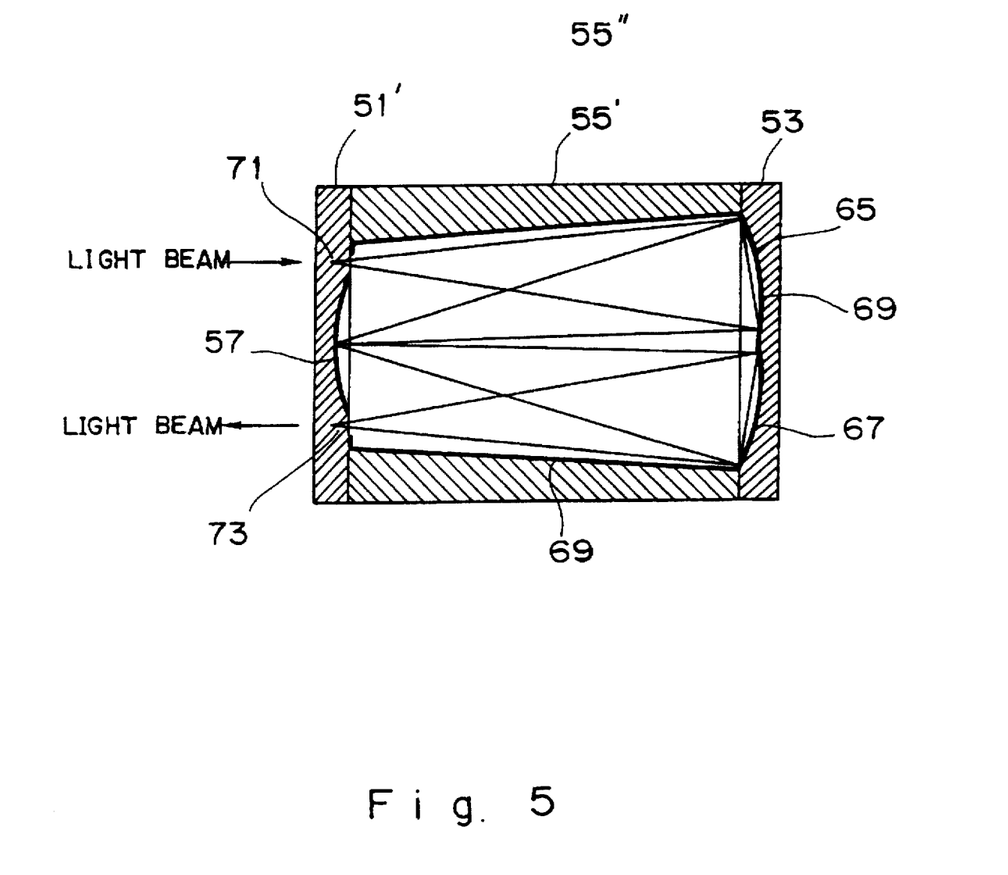
FIG. 5 is a cross-sectional view of a third embodiment of a sample cell of multiple reflection type according to the invention.

FIG. 5 is a cross-sectional view of a third embodiment of a sample cell 50" of multiple reflection type according to the invention. This sample cell 50" comprises a mirror plate 51', the side plate 53 and the frame 55'. Same reference numerals denote the same members in FIGS. 2 through 5.

As shown in FIG. 5, the mirror plate 51', which includes the central concave mirror 57 and light incident and exit portions 71 and 73, is made of a material transparent with respect to the infrared wavelengths used for analytical measurement.

In the third embodiment, crystalline silicon is used for the mirror plate 51'. Crystalline silicon is transparent in infrared regions and can be easily and finely worked (formed) by a micro-machining technique of, for example, etching. Sapphire and calcium fluoride may be used in place of crystalline silicon as the transparent material for the mirror plate 51'. When a near-infrared ray is used for analysis, some optical glasses and engineering plastics may be used as the transparent material.

Though it is not always necessary to use the same material for the side plate 53 and the frame 55' with that of the mirror plate 51', the mirror plate 51', the side plate 53 and the frame 55' are made of crystal silicon in the third embodiment, since the same machining techniques, including precision bonding such as electrostatic bonding, may be effectively utilized.

The concave mirrors 57, 65, and 67 and holes are formed on crystalline silicon by the micro-machining techniques such as etching and grinding. Reflection and shading planes are formed on the region 69 indicated by thick bold lines in FIG. 4, which correspond to the inner surfaces of the sample cell excluding the light incident and exit portions 71 and 73 and the bonding faces of the constituent parts 51', 53 and 55'. The reflection and shading planes are formed by depositing highly reflective metal or highly refractive material by vacuum deposition, sputtering and such deposition techniques. The constituent parts are precisely bonded, with the bonding faces thereof in tight contact, by electrostatic bonding, to be the sample cell 50" of multiple reflection type.

Since the refractive index of crystalline silicon is around 3 which is sufficiently high and results in high reflectivity of the silicon crystal mirror plate 51', the light beam passing through the mirror plate 51' becomes only around 50% of the incident light beam launched into the mirror plate 51'. The optical transmittance of the mirror plate 51' can be improved to nearly 100% to further improve the efficiency of analysis in the sample cell by coating the outside surface and/or inside surface of the light incident and exit portions 71 and 73 of the mirror plate 51' with antireflection films.

The antireflection film is made of a transparent material such as $MgF_2$ with a lower refractive index than that of crystalline silicon, and deposited so as to be a quarter (¼) as thick as the used wavelength. In addition, the thin films constituting the light incident and exit portions 71 and 73 may be formed to be optical band pass filters, either low pass filters or high pass filters, by laminating multiple transparent layers having different refractive indices from one another. By forming the optical band pass filters, the wavelengths of the light which enters the detector and the sample cell are confined within a narrow range to be used for the analysis and a high S/N ratio is obtained in the detection signals.

As explained above, the sample cell of multiple reflection type according to the invention is based on the principle of the White cell which essentially comprises three concave mirrors and light incident and exit windows. The concave mirrors and windows are formed on the constituent wall surfaces of the sample cell by micro-machining within the predetermined precision which satisfies the given optical conditions. The sample cell is assembled by tightly bonding the end wall parts, including the concave mirrors, with the respective ends of the frame as the side wall part which determines the spacing between the concave mirrors. Therefore, it becomes unnecessary to dispose adjusting mechanisms for finely adjusting the positions and orientations of the concave mirrors in the sample cell, and the dimensions of the sample cell having a long optical path are minimized.

The thus constructed small and compact sample cell of multiple reflection type is especially suited for the nondispersive infrared gas analyzers and such analyzers for detecting a low concentration component. Many replicas of the constituent parts can be manufactured at low manufacturing cost by compression molding, and the sample cell of the invention can be assembled by tightly bonding the constituent molded parts with each other.

By occupying the space immediately beyond of the envelope region of the light beams in the sample cell with the frame which defines the inside wall of the sample cell, any dead space is left in the sample cell and the sample cell dimensions are minimized. Therefore, the sample gas can be replaced quickly, and a high response speed is realized in the ultraviolet gas analyzer and such analyzers which adopt the sample cell of the invention. At least one of the light incident and exit windows (or portions), formed to be an optical band pass filter of a low pass filter or a high pass filter, which passes only the absorption wavelength of a component to be analyzed, by laminating multiple layers having different refractive indices from one another, facilitates highly precise measurement of the component by avoiding interference from coexisting components.

By using crystalline silicon, transparent in the ultraviolet region for the mirror plate on which the central concave mirror is formed and for the other parts, the constituent parts are simplified, since it is not necessary to form any light incident and exit windows individually. Since various micro-machining techniques such as etching, precision grinding and electrostatic bonding are applicable in machining a silicon crystal, a minute multiple-reflection sample cell having a long optical path is realized, and a small but compact nondispersive infrared gas analyzer is obtained for measuring a low concentration component.

What is claimed is:

1. A sample cell of the multiple reflection type in which incident light is reflected a plurality of times, for analyzing a sample in the sample cell, comprising:

a mirror plate including a light incident window for introducing the incident light into the sample cell, a first concave mirror, and a light exit window for outputting the incident light from the sample cell;

a side plate including a second concave mirror for reflecting the incident light to the first concave mirror, and a third concave mirror for reflecting the incident light reflected by the first and second concave mirrors to the light exit window; and a frame for fixing the mirror plate and the side plate so that distances between the first concave mirror and the second and third concave mirrors are fixed.

2. The sample cell according to claim 1, wherein the distance between the first concave mirror and the second and third concave mirrors corresponds to the radius of curvature of the first, second and third concave mirrors, the second concave mirror focuses an image of the light incident window on the first concave mirror, and the third concave mirror focuses on the light exit window an image focused on the first concave mirror.

3. The sample cell according to claim 1, wherein the second and third concave mirrors are integrated with the side plate in one piece.

4. The sample cell according to claim 1, wherein the frame occupies a space immediately beyond the envelope region within which the incident light passes in the sample cell.

5. The sample cell according to claim 1, wherein one of the mirror plate, the side plate and the frame is made of one of aluminum and aluminum alloy.

6. The sample cell according to claim 1, wherein a chrome (Cr) layer, a silicon dioxide ($SiO_2$) layer, and a gold (Au) layer are formed in this order on an inside wall of the sample cell.

7. The sample cell according to claim 1, wherein one of the mirror plate, the side plate and the frame is a replica duplicated using a molding die.

8. The sample cell according to claim 1, wherein two of the mirror plate, the side plate, and the frame are respectively paired and molded in one piece prior to assembly.

9. The sample cell according to claim 1, wherein the light incident window comprises a transparent substrate and a transparent layer formed on the transparent substrate, refractive indices of the transparent substrate and the transparent layer being different from each other, and the transparent substrate and the transparent layer function as an optical band pass filter.

10. The sample cell according to claim 1 wherein the light incident window comprises a plurality of transparent layers having different refractive indices and functions as an optical band pass filter.

11. The sample cell according to claim 1, wherein the light exit window comprises a transparent substrate and a transparent layer formed on the transparent substrate, refractive indices of the transparent substrate and the transparent layer being different from each other, and the transparent substrate and the transparent layer function as an optical band pass filter.

12. The sample cell according to claim 1, wherein the light exit window comprises a plurality of transparent layers having different refractive indices and functions as an optical band pass filter.

13. The sample cell according to claim 1, wherein the mirror plate is made of a material transparent with respect to wavelengths of light used for an analysis of the sample, and a layer of a material having one of high reflectivity and high refractive index is formed on a portion of the mirror plate corresponding to the first concave mirror.

14. The sample cell according to claim 13, further comprising
an antireflection film, having a refractive index smaller than that of the mirror plate, formed on a portion of the mirror plate corresponding to the light incident window.

15. The sample cell according to claim 13, further comprising
an antireflection film, having a refractive index smaller than that of the mirror plate, formed on a portion of the mirror plate corresponding to the light exit window.

16. The sample cell according to claim 13, further comprising
a transparent layer formed on a portion of the mirror plate corresponding to the light incident window, wherein refractive indices of the transparent layer and the mirror plate are different from each other, and the transparent layer and the portion of mirror plate function as an optical band pass filter.

17. The sample cell according to claim 13, further comprising
a plurality of transparent layers formed on a portion of the mirror plate corresponding to the light incident window, wherein refractive indices of the plurality of transparent layers are different from each other, and the plurality of transparent layers function as an optical band pass filter.

18. The sample cell according to claim 13, further comprising
a transparent layer formed on a portion of the mirror plate corresponding to the light exit window, wherein refractive indices of the transparent layer and the mirror plate are different from each other, and the transparent layer and the portion of mirror plate function as an optical band pass filter.

19. The sample cell according to claim 13, further comprising
a plurality of transparent layers formed on a portion of the mirror plate corresponding to the light exit window, wherein refractive indices of the plurality of transparent layers are different from each other, and the plurality of transparent layers function as an optical band pass filter.

20. A manufacturing method of a sample cell of multiple reflection type in which incident light is reflected a plurality of times for analyzing a sample in the sample cell, including the steps of:
manufacturing a mirror plate including, a light incident window for introducing the incident light into the sample cell, a first concave mirror, and a light exit window for outputting the incident light from the sample cell;
manufacturing a side plate including, a second concave mirror for reflecting the incident light to the first concave mirror, and a third concave mirror for reflecting the incident light reflected by the first and second concave mirrors to the light exit window; and
manufacturing a frame for fixing the mirror plate and the side plate so that the distances between the first concave mirror and the second and third concave mirrors are fixed.

21. The manufacturing method according to claim 20, wherein
the distance between the first concave mirror and the second and third concave mirrors corresponds to the radius of curvature of the first, second and third concave mirrors, the second concave mirror is formed so as to focus an image of the light incident window on the first concave mirror, and
the third concave mirror is formed so as to focus on the light exit window an image focused on the first concave mirror.

22. The manufacturing method according to claim 20, wherein
the second and third concave mirrors are integrated with the side plate in one piece.

23. The manufacturing method according to claim 20, wherein
the step of manufacturing the side plate includes a step of making the second and third concave mirrors by cutting the side plate using a lathe.

24. The manufacturing method according to claim 20, wherein
the side plate, including the second and third concave mirrors, is molded in one piece using a die.

25. The manufacturing method according to claim 20, wherein
the mirror plate and the frame are molded in one piece using a die.

26. The manufacturing method according to claim 20, wherein
the frame is manufactured so that an inside space of the frame broadens along the direction from the mirror plate to the side plate.

27. The manufacturing method according to claim 20, further including the step of
forming a chrome (Cr) layer, a silicon dioxide ($SiO_2$) layer and a gold (Au) layer in this order on an inside wall of the sample cell.

28. The manufacturing method according to claim 20, further including the steps of,
attaching a transparent plate to the light incident window, and
forming, on the transparent plate, a transparent layer having a refractive index different from that of the transparent plate.

29. The manufacturing method according to claim 20, further including the step of
forming, at the light incident window, a plurality of transparent layers having refractive indices different from each other.

30. The manufacturing method according to claim 20, further including the steps of,
attaching a transparent plate to the light exit window, and
forming, on the transparent plate, a transparent layer having a refractive index different from that of the transparent plate.

31. The manufacturing method according to claim 20, further including the step of
forming, at the light exit window, a plurality of transparent layers having refractive indices different from each other.

32. The manufacturing method according to claim 20, wherein
the mirror plate is made of a material transparent with respect to wavelengths of light used for an analysis of the sample, and
the manufacturing method further includes the step of forming a layer of a material having one of high reflectivity and high refractive index, on a portion of the mirror plate corresponding to the first concave mirror.

33. The manufacturing method according to claim 32, further including the step of forming an antireflection film, having a refractive index smaller than that of the mirror plate, on a portion of the mirror plate corresponding to the light incident window.

34. The manufacturing method according to claim 32, further including the step of forming an antireflection film, having a refractive index smaller than that of the mirror plate, on a portion of the mirror plate corresponding to the light exit window.

35. The manufacturing method according to claim 32, further including the step of forming a plurality of transparent layers on a portion of the mirror plate corresponding to the light incident window, refractive indices of the plurality of transparent layers being different from each other.

36. The manufacturing method according to claim 32, further including the step of forming a plurality of transparent layers on a portion of the mirror plate corresponding to the light exit window, refractive indices of the plurality of transparent layers being different from each other.

* * * * *

UNITED STATES PATENT AND TRADEMARK OFFICE
CERTIFICATE OF CORRECTION

PATENT NO. : 5,726,752
DATED : March 10, 1998
INVENTOR(S) : Uno et al.

It is certified that error appears in the above-identified patent and that said Letters Patent is hereby corrected as shown below:

Column 1, line 9, before "sample" insert

--type--

Column 1, line 10, delete "of"

Column 1, line 16, delete "thereof" and insert --to-- therefor

Column 1, line 38, after "cell" insert --of--

Column 1, line 54, before "exit" insert --an--

Column 7, line 32, delete "dimension" and insert --the light-- therefor

UNITED STATES PATENT AND TRADEMARK OFFICE
CERTIFICATE OF CORRECTION

PATENT NO.   : 5,726,752
DATED        : March 10, 1998
INVENTOR(S)  : Uno et al.

It is certified that error appears in the above-identified patent and that said Letters Patent is hereby corrected as shown below:

Column 8, line 64, delete "of"

Signed and Sealed this

Fifteenth Day of September, 1998

Attest:

BRUCE LEHMAN

*Attesting Officer*           Commissioner of Patents and Trademarks